US 11,538,567 B2

(12) United States Patent
    Davies

(10) Patent No.: US 11,538,567 B2
(45) Date of Patent: Dec. 27, 2022

(54) EXPERT REPORT EDITOR

(71) Applicant: INTEX HOLDINGS PTY LTD, Collinswood (AU)

(72) Inventor: Roger Davies, Collinswood (AU)

(73) Assignee: INTEX HOLDINGS PTY LTD

( * ) Notice: Subject to any disclaimer, the term of this patent is extended or adjusted under 35 U.S.C. 154(b) by 0 days.

(21) Appl. No.: 17/054,720

(22) PCT Filed: May 14, 2019

(86) PCT No.: PCT/AU2019/050452
    § 371 (c)(1),
    (2) Date: Nov. 11, 2020

(87) PCT Pub. No.: WO2019/218005
    PCT Pub. Date: Nov. 21, 2019

(65) Prior Publication Data
    US 2021/0166796 A1    Jun. 3, 2021

(30) Foreign Application Priority Data

| May 15, 2018 | (AU) | ................................ 2018901680 |
| Oct. 2, 2018 | (AU) | ................................ 2018903717 |
| Apr. 10, 2019 | (AU) | ................................ 2019901229 |

(51) Int. Cl.
    *G06F 17/00*      (2019.01)
    *G16H 15/00*      (2018.01)
    *G06F 40/186*     (2020.01)

(52) U.S. Cl.
    CPC .......... *G16H 15/00* (2018.01); *G06F 40/186* (2020.01)

(58) Field of Classification Search
    CPC .......... G06F 40/186; G06F 7/00; G06F 40/10; G06F 40/174; G06F 16/248; G06F 3/0237; G06F 40/166; G06F 40/274; G06F 40/131; G16H 15/00; G16H 10/60; G16H 30/20; G16H 30/40; G06N 3/00; G06N 20/00; G16B 50/00; G06T 7/00; G06T 2207/30004; G06T 7/0012
    See application file for complete search history.

(56) References Cited

U.S. PATENT DOCUMENTS 5,953,011 A *   9/1999  Matsuoka ............... G06F 9/453
                                                    715/764
7,610,192 B1 * 10/2009  Jamieson ............... G16H 10/60
                                                    705/2

(Continued)

FOREIGN PATENT DOCUMENTS

WO        2017189758        11/2017

*Primary Examiner* — Laurie A Ries
(74) *Attorney, Agent, or Firm* — Sand, Sebolt & Wernow Co., LPA

(57) ABSTRACT

A radiological report editor that takes advantage of a series of templates for different types of reports. The templates provide appropriate statements which can be inserted and modified in accordance with specific observations. The statements are presented to the user in the order in which they would typically appear in a report. The statements may contain grammatically interchangeable qualifiers presented to the user in the order of historical statistical usage. A report can be based on previous reports chosen to best match the metadata of the new report, or best matching the image being reported.

34 Claims, 2 Drawing Sheets

(56) References Cited

U.S. PATENT DOCUMENTS

| | | | | |
|---|---|---|---|---|
| 7,908,293 B2* | 3/2011 | Aronson | | G16H 10/40 707/791 |
| 8,630,970 B2* | 1/2014 | Bryce | | G16H 15/00 706/47 |
| 10,061,763 B2* | 8/2018 | Tamilarasan | | G06F 40/186 |
| 10,762,168 B2* | 9/2020 | Qian | | G16H 15/00 |
| 10,777,307 B2* | 9/2020 | Schulze | | G16H 15/00 |
| 11,152,084 B2* | 10/2021 | Kondadadi | | G16Z 99/00 |
| 2008/0104116 A1* | 5/2008 | Van Hoe | | G06T 7/0012 |
| 2009/0150771 A1* | 6/2009 | Buck | | G16H 15/00 715/273 |
| 2010/0153881 A1* | 6/2010 | Dinn | | G06F 3/0237 715/825 |
| 2011/0307435 A1* | 12/2011 | Overell | | G06F 16/3329 706/46 |
| 2012/0176408 A1 | 7/2012 | Moriya | | |
| 2013/0144605 A1* | 6/2013 | Brager | | G06F 40/40 704/9 |
| 2013/0251233 A1* | 9/2013 | Yang | | G16H 30/20 382/132 |
| 2013/0339358 A1* | 12/2013 | Huibers | | H04L 51/32 707/737 |
| 2014/0013199 A1 | 1/2014 | Buurman | | |
| 2014/0278448 A1* | 9/2014 | Sadeghi | | G06Q 10/10 705/2 |
| 2015/0310115 A1* | 10/2015 | Ryger | | G06F 16/24578 707/708 |
| 2016/0034578 A1* | 2/2016 | Wang | | G06Q 40/08 707/722 |
| 2016/0364445 A1* | 12/2016 | Golec | | G06Q 10/10 |
| 2017/0053074 A1* | 2/2017 | Enzmann | | G06T 7/0012 |
| 2017/0199189 A1* | 7/2017 | Wade | | G01N 33/50 |
| 2017/0286388 A1* | 10/2017 | Tamilarasan | | G06F 16/248 |
| 2017/0337329 A1 | 11/2017 | Liu et al. | | |
| 2018/0301222 A1* | 10/2018 | Dew, Sr. | | G06F 16/9577 |
| 2019/0220978 A1* | 7/2019 | Moehrle | | G06T 7/0014 |
| 2019/0266243 A1* | 8/2019 | Farooq | | G16H 50/20 |
| 2022/0020495 A1* | 1/2022 | Sadeghi | | G06F 40/143 |

* cited by examiner

EXPERT REPORT EDITOR

FIELD OF THE INVENTION

The present invention relates to an editor for generating expert reports based on observations. It is specifically targeted towards radiology reports but is also applicable to report generation in other fields.

BACKGROUND TO THE INVENTION

The invention provides a report editor to quickly generate reports which are essentially a list of observations, logically derived conclusions and recommendations. The invention was developed to target radiology reports and will be discussed in such a context, but it is to be understood that the invention is applicable across a wide range of technical areas where reports are comparable, i.e. observations, logically derived conclusions and recommendations.

A radiology report typically includes a patient history; details of the imaging technique used; details of findings; conclusions; and recommendations. Such a report requires the skill of a radiologist to generate and can often take up to 15 minutes to produce using conventional word processing tools, or even longer depending on the language skills of the radiologist. Reports for a specific body part and technique are often repetitive, i.e. having the same or similar observations and conclusions, particularly for patients with similar demographics and presenting with similar symptoms. However many observations and hence reports include subtle variations from the norm. Similarities in radiological images also lead to repetitive observations and conclusions.

Traditional radiology reporting systems are based on dictation and transcription or voice recognition to convert a synthesis of image observations, and prior knowledge of anatomy, pathology and imaging diagnosis, dictated by the radiologist, to constitute a final report and image interpretation. This method relies on the (fallible) memory and (limited) knowledge of the reporting radiologist and an (error prone) transcription process to produce a written report which is intended to add value to the images that can otherwise be directly interpreted by another health practitioner. Restrictions of this method include the vagaries of verbal expression being inexact, prone to inter-observer variation and not readily amenable to form precise input data for any machine learning algorithm intended to improve image interpretation, without further classification, characterization or codification.

Pro forma or template based reporting modules improve on the traditional reporting strategies by reducing the inexact reporting expression problem but suffer from rigidity of style, a limited range or cumbersome language, complexity of template selection and the large number of permutations that human pathology can manifest when imaged, resulting in a 'square peg in round hole' phenomenon for traditional template based description systems. Traditional templates do not address limited knowledge and fallible memory. So called boiler plate templates have limited or no capacity to adjust to the reporting preferences of each radiologist.

Many radiological practises maintain a collection of past reports for use as templates for new reports. Due to the variations in observations it is impractical to have complete templates for each pathology, or combination of pathologies, and considerable time is still required to generate a report. Maintenance of such template collections is an onerous task as corrections or improvements in a standard term or phrase may require amendment to multiple documents.

Advances in the understanding of disease, or new treatment strategies involving imaging, may be overlooked once training is complete, without a suitable addition to the template knowledge base. Templates typically provide no feedback to the user in the form of teaching or training.

Because of the lack of precision by the reporting radiologist, dictated reports are frequently open to misinterpretation. Most metadata available to assist in formulation of a report and opinion are only utilized by the reporting radiologist to a limited degree, based on recalled knowledge.

The object of this invention is to provide a report editor that takes advantage of similarities in radiological data to speed up report generation whilst facilitating recording of individual variations, or at least provide the public with a useful alternative.

SUMMARY OF THE INVENTION

In a first aspect the invention comprises an editor for generating a report about an image from a template, wherein the template comprises a series of statements selectively included in the report from a database.

Preferably the statements comprise selectable qualifiers which alter the meaning of the statements and the qualifiers are presented for selection in order based on an associated probability of selection. Preferably the probability of selection of a qualifier is updated when a qualifier is selected.

In preference the reports are stored in a database, and a new report may be based on a report selected from the stored reports, and the selection of statements in the new report is copied from the selection of statements in the selected report.

The user may select which stored report to base the new report on, and may base a new report on selections from multiple stored reports.

The user is preferably presented with a selection of stored reports from which the new report is based on, the stored reports presented in order of a score, the score being determined by matching metadata of the new report with metadata of the stored reports, or the score being determined by matching the image of the new report with the images of the stored reports.

The statements may be presented in order corresponding to the probability that the statement is likely to be selected based on the selection of statements in historical reports. The probability that a statement will be selected may be based on the selection of other statements, or based on the selection of pairs of other statements.

It should be noted that any one of the aspects mentioned above may include any of the features of any of the other aspects mentioned above and may include any of the features of any of the embodiments described below as appropriate.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF THE INVENTION

Figure 1:
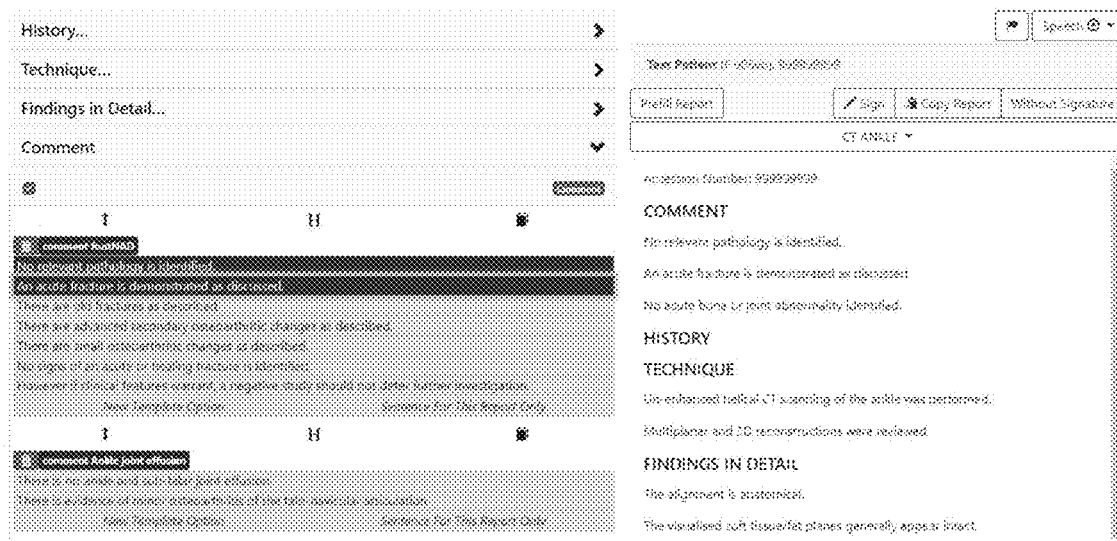
FIG. 1 shows a partial screenshot of the editor of the invention showing the statement selection pane (middle pane) and radiological report (right pane) as produced by the invention.

The following detailed description of the invention refers to the accompanying drawings. Wherever possible, the same reference numbers will be used throughout the drawings and the following description to refer to the same and like elements.

The present invention provides a novel reporting system using a machine learning algorithm that has been developed to address the limitations of prior art manual and semi-automated processes to increase productivity and reduce opportunities for error. In developing a practical implementation of the system an AI learning algorithm was applied to a very large database of >150,000 sentence variations derived from more than 500,000 reported studies which contain a fixed stem and modifiers to amend or qualify the meaning of a sentence. This sentence bank covers more than 99% of events in a library of reported imaging studies. The sentences are grouped in a consistent manner into a library of topic-based report building blocks. These reporting blocks are utilized in one, several or many report types as appropriate. Every sentence or group of sentences is categorized and indexed to allow automated retrieval. The patterns of utilization are exactly analysed and the likelihood of sentences being used in combination and the order in which they are used enters a mathematical array that learns and revises the computed probability of utilization with every new completed report.

AI based on metadata analysis of the patient (age, sex, presenting symptoms, clinical diagnosis, physical examination) and the reporting patterns of the radiologist is used to predict the sentences required for each new imaging study. The prediction algorithm uses a novel prediction strategy to accurately predict rarely used combinations of sentences as well as common usage patterns. The less often a particular statement occurs the more likely it is that other statements within the common report are correlated. If a statement has been used in a single instance, then each other statement within that report will have a frequency ratio of 100% with respect to that statement.

Each reported study has extensive additional metadata based on codes derived from the sentences bank items utilized in the report. An image similarity score is derived from a computed comparison with prior images coded with the same sentence bank. This similarity score is used to further refine the probability of sentences being used in a specific study to be reported.

Where a trainee uses the predicted sentence pattern and modifies these to produce a draft report, an experienced radiologist may more rapidly complete the report analysis, easily modifying the selected sentences because these are presented with standardized phraseology, in a standardized order, with all users accessing an interface based on standard web based technology and a cloud based store of sentence metadata. The experienced reporter's modifications are stored in entirety to allow the trainee to receive complete feedback on their draft, resulting in a comprehensive learning event log for every report attempted being available to the trainee. Trainees rapidly improve to achieve 90-100% accuracy in the generation of draft reports.

The web interface is interactive, presenting the draft sentence data in a variety of formats with extensive navigational aids to facilitate very rapid access to and modification of selected sentences by limited key strokes and very limited mouse clicks for most operations. Sentence selections are continuously modified as sentences are selected or rejected by the reporting radiologist to optimise report accuracy and minimize time to completion.

Anonymized metadata from each completed report is added to the sentence metadata library and used by the machine learning algorithm to better predict the content of future similar reports.

Additional sentences can be added to sentence groups, and new sentence groups can be added and combined with exiting sentence bank elements to expand the range of modalities and range of imaging studies covered by the reporting system.

The system continuously learns from and improves sentence prediction based on prior utilization patterns. Rare or unique usage patterns are recalled as accurately as more common or very common usage patterns due to the novel selection algorithm using the frequency of co-occurrence, in preference to the overall frequency of occurrence of a sentence.

A preferred embodiment of the invention provides a radiological report editor that takes advantage of a series of templates for different types of reports. The templates provide appropriate statements which can be inserted and in many cases modified in accordance with specific observations. The statements are presented to the user in the order which they would typically appear in a report, allowing the user to scroll down the list of statements and select relevant statements. Some statements can be modified by the selection of alternative qualifiers, e.g. small/medium/large, chosen from a dropdown list with the default option presented being the most likely choice based on the selections made in previous reports. Each statement in the report is expressed in the same matter to make the reports more readable and allow for machine analysis. Reports may also be based on previous reports, selected according to report metadata or image comparison. Preferably each new report adds to the corpus of historical reports with statistical observations allowing each new report to take advantage of previous reports.

Before describing the invention, the structure of a report generated by the system will be described. The invention will be described first from a functional perspective by describing the user interaction with the system to generate a report.

Whilst a radiology report can take many forms, describe a huge variety of medical conditions and various imaging techniques, the format of a report can be normalised to allow for machine generation and editing. For the invention a report format as per the right hand side of FIG. 1 has been chosen, which includes sections for a title, comment, history, technique and findings in detail. The Title Section briefly identifies the type of study; the Comment Section provides a summary of key findings and conclusions that can be drawn from them; the History Section provides a medical history of the patient; the Technique Section describes the imaging undertaken; and, the Findings In Detail Section is a series of statements detailing observations from the study. The invention helps a radiologist generate the various sections of the report. The title, history and technique sections are readily generated from report metadata and will not be discussed in detail. The focus of the invention is in populating the findings in detail and comments sections which comprise a series of standardised statements selected and modified by the radiologist.

When generating a report the user is presented with a series of standardised statements that can be included in the report, such as "There is some evidence of degeneration". Usually one or more phrases in the statement are replaceable by other grammatically interchangeable phrases. In this instance the phrase "some" is interchangeable with any phrase selected from "no/some/weak/strong". The various statements presented to the user can be included or not as desired and moved within the report. The use of selectable statements minimises or even eliminates typing, speeding up report generation, particularly for people with disabilities or poor English language skills. Statements have metadata, e.g. default selection. Selected statements in the findings in detail section can be tagged as key observations so that they will also appear in the comment section.

To begin a new report the metadata for the report is entered into the editor, either from a compatible management program, or manually by the user using a selection of conventional GUI components. The metadata includes: patient demographic details such as age and sex; patient medical history; study details, i.e. type of imaging and target area, e.g. chest X-ray; and management information such as date and clinician details.

Once the metadata has been entered a template can be loaded. A template is available for each type of study, e.g. Chest X-ray, and contains statements appropriate to that study.

Alternatively to using a template to generate a new report, a new report may be based on a previous report. The user may either browse previous reports; search for reports by keywords or search for reports based on metadata. Once an initial selection of candidate reports has been identified the images from those reports can be compared to the image for the current report to refine the selection.

To search for reports based on metadata, the user selects which metadata criteria to base the search on and gives a weighting to each of the criteria. For example, when starting a report for a knee x-ray for a sporting injury the user would most likely choose to search based on study type and age of the patient and giving a higher weighting to the study type. Metadata used to match previous reports includes study type, age and, sex. A weighting can also be given to the age of previous reports as newer reports in the system tend to be more accurate as they have taken advantage of the system as it improves over time. A score for each report is generated based on the degree of metadata matching and the weighting given to the metadata. A list of reports is presented to the user in order of the scores generated.

When searching based on image matching, the image of the present study is compared to images of previous comparable studies using an image matching algorithm. The algorithm does not need to recognise any elements of the image, it just needs to give a score as to the degree of match. The image matching score can be used alone, or in combination with the metadata matching score. The chosen scoring regime is then used to determine the order of reports presented to the user to choose from.

The candidate reports are presented as list which includes selected metadata and the scores for the user to browse. On selecting a candidate report from the list the contents of the report is shown to the user. The user can then select all of or just a selection of statements in the report to include in the new report. Statements from multiple previous reports may be included in the new report. This is particularly useful where multiple pathologies are present.

Once a template, previous report, or a combination of statements from multiple previous reports has been chosen the editor presents the user with a 3 pane interface. In general the left hand pane contains search and navigation aids, the middle pane provides a series of statements that can be selected as content of the report, and the right hand pane shows a preview of the report made from selected statements. The middle and right hand panes are shown in FIG. 1.

When a template is loaded to generate a report several statements are selected by default and populate the report. These typically correspond to normal morphology. To add statements to the report the user first selects the section of the report to edit enabling the display of statements to select from. Related statements are typically grouped together in subsections. In FIG. 1 the Comment Section has been selected showing a non-expanded first subsection and an expanded second subsection. Clicking on a non-expanded subsection will expand it and un-expand the other subsections. Clicking on the statements within the subsection will add them to the corresponding section of the report.

As a report is being edited and the user selects a statement in the report the template pane is automatically updated to show the section and subsection of the template that the statement came from. This facilitates adding statements from the same section and is particularly useful when revising a report, or when creating a report based on previous reports.

Figure 2:
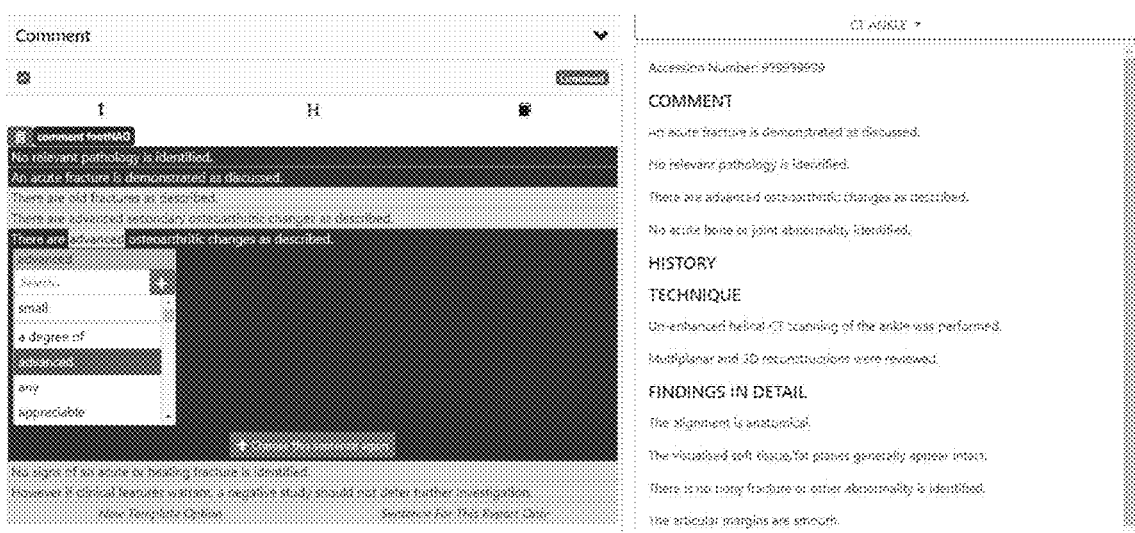
FIG. 2 shows the statement selection pane middle pane of the editor with a section expanded to show a statement with a qualifier expanded.

FIG. 2 shows the editor with a statement selected, "There are advanced osteoarthritic changes as described", that includes a qualifier "advanced". The qualifier is highlighted for easy identification by the user. On bringing focus to a qualifier a drop down list of alternative qualifiers is presented to select from, with the alternatives presented in order corresponding to the probability that they will be selected. Upon selection of a qualifier the statement is updated in the Editor Section and the Report Section. The probability of selection of the qualifiers is stored in the template and updated each time that a qualifier is selected. Each time the template is used it will improve the accuracy at which it presents the qualifiers.

As a report is being generated a background process analyses the statements selected for consistency and redundancy. This is achieved by comparing the text and metadata of selected statements against each other and with the metadata of the report. For example, if a statement from a subsection is selected and that statement is flagged in its metadata as a default statement, which is usually the case for normalcy, then a further selected statement from the same subsection which is not flagged in its metadata as a default statement would be highlighted as potentially erroneous.

The editor also provides logins for different users and tracks the activity of each user. The editor interface includes a count of changes made to a report by each user and can highlight additions, deletions or modifications by each user on a user by user basis. Typically a report will be reviewed by a senior radiologist, and the number of changes needing to be made by them provides a good measure of the accuracy of the initial editor. On revisiting the report after it has been reviewed, the initial editor can view the changes made and thus learn from the reviewing radiologist.

The editor has been discussed from a user perspective, but may also be used in an administrative mode in which the selectable statements and replaceable phrases may be edited. Typically if an appropriate statement is not available a new one is added by a supervisor to cater for the report at hand and also to be available to future reports. If needed a user may also add free text to the various sections of the report.

The standardised statements presented to the user for selection are presented in order of their probability of selection, the probability being derived from a prediction strategy based on historical reports. The prediction strategy consists of three distinct elements: first, a database which accounts for the relative frequency of statements occurring within common reports; secondly, some means for providing some initial statements, from which the predictions can be generated; and, thirdly, a method for determining from multiple distinct relative frequencies, for each statement within a vector comprised of available statements, an aggregated chance of each statement also occurring in conjunction with the selected statements.

The first element of the prediction strategy is a database, or frequency array, which accounts for the relative frequencies of statements, containing the chance that if a report contains one statement then it also includes another i.e. the value (j, k) represents the likelihood of k appearing in a report that also contains j. It therefor is a square array of magnitude equal to the number of unique statements, or a vector of length equal to the number of statements, where each element is a vector of the same length.

To create the frequency array, find the frequency vectors corresponding to each statement. For each statement j, return all the reports containing j. For every other statement k, the frequency corresponding to k is the ratio of the number of incidences of k within the returned reports to the number of returned reports. For example, if j occurs in 10 reports, and k occurs in 2 of those reports, then (j, k)=0.2, regardless of how many times k occurs within all reports. This can be extended to statement pairs, i.e. following the above procedure but replacing j with a pair i, j. This provides for a greater robustness between discovered associations at the expense of a much larger database and of computational requirements.

The second element of the prediction strategy is the use of initial statements, or seed statements, in order to generate predictions. This has been done by matching key words within the sentences to classify statements by anatomical feature or pathology. This is a simple approach and the resultant classification lists are incomplete and inaccurate, but sufficient for purpose. By using these classified statements as inputs, and checking the resultant predictions against the reports in which the input statement occurs, an average predictive accuracy is found. This is the average proportion of those statements within the report which are also found within the predictions.

With the valid values for the two classification types selected, an array is created to give the predictions which have been shown to be of the greatest utility. First, the twenty highest rated statements for each classification type are found. The top three from each are inserted as the first six elements of a new vector, when there are less than three statements within a classification type then the corresponding vector elements are left empty. The remaining elements of the vector are filled in turn with the most predictive statements from either classification type.

Use of the paired matrix shows potential for the generation of seed statements as the statements pairs which correspond to the selected classification inputs are easily established, this could also be extended to other forms of metadata such as age, history, gender, or any other information which can be maintained with the statements.

The third element of the prediction strategy is to determine the probability of each statement also occurring in conjunction with the selected statements. For each statement, the predictions correspond to the statements with the highest frequency ratio. If all reports containing a chosen statement also contain a second statement, then the frequency ratio for the second statement should be 1 and this statement returned as a prediction. For n desired predictions, the statements corresponding to the nth highest prediction ratios are returned. When multiple statements are used as the basis for generating predictions, then a vector formed by averaging the corresponding prediction ratios is created and the predictions returned from the highest average ratios.

This method is of most utility when the values used as a basis for prediction have a relatively low overall frequency of occurrence within the full set of reports, as the less often a particular statement occurs the more likely it is that other statements within the common report are correlated in some way. If a statement has been used in a single instance, then each other statement within that report would have a frequency ratio of 1 with respect to that statement, and if it were used as an input then the predicted output would be that previous report. Conversely, if a statement which occurs in nearly all reports were used as the only input, then the returned predictions would be in essence a list of the most common statements.

The preferred embodiment of the invention includes a client application to generate the user interface and provide various services such as proofreading, and a server application for storing and retrieving reports and templates from a database. The implementation of the client and server applications may take a variety of forms as is well known in the art of computer science. More relevant to the invention than programming details are the structure of the reports and templates, and associated metadata.

The reader will now appreciate the present invention which provides a report editor which facilitates quick report generation. A user can in most instances generate a report without the need to type anything, and as the user is prompted by a myriad of available statements they are also likely to produce more accurate reports than they would have otherwise. As the system accumulates reports over time it will be able to deliver better matching reports to base new reports on, and present statement qualifiers in the order in which they are most likely to be selected.

Further advantages and improvements may very well be made to the present invention without deviating from its scope. Although the invention has been shown and described in what is conceived to be the most practical and preferred embodiment, it is recognized that departures may be made therefrom within the scope of the invention, which is not to be limited to the details disclosed herein but is to be accorded the full scope of the claims so as to embrace any and all equivalent devices and apparatus. Any discussion of the prior art throughout the specification should in no way be considered as an admission that such prior art is widely known or forms part of the common general knowledge in this field.

In the present specification and claims (if any), the word "comprising" and its derivatives including "comprises" and "comprise" include each of the stated integers but does not exclude the inclusion of one or more further integers.

The invention claimed is:
1. A report editor comprising:
a non-transitory computer readable storage medium; and
a database operatively engaged with the non-transitory computer readable storage medium;
wherein the non-transitory computer readable storage medium stores instructions for generating a report about an image from a template;

wherein the template comprises a series of statements selectively included in the report from the database;

wherein the database stores a plurality of reports including historical reports;

wherein a new report generated by the non-transitory computer readable storage medium is based on a selected report from the plurality of reports stored in the database;

wherein a selection of the series of statements in the new report is copied from a selection of statements in the selected report or from multiple stored reports;

wherein the series of statements are presented in order corresponding to a probability that any particular statement is likely to be selected;

wherein the probability that the particular statement is selected is based on a selection of a first statement and a frequency of selection of a second statement when the first statement has been selected in the historical reports; or is based on the selection of a pair of statements and the frequency of selection of the second statement when the pair of statements has been selected in the historical reports;

wherein the selected series of statements in the new report are edited and the edited statements are stored in the database;

wherein the edited statements are included in a completed report and the completed report is stored in the database;

wherein the stored edited statements and the stored completed report update the database and are made available for use in a subsequent template for a subsequent new report; and wherein anonymized metadata from each completed report is added to a statement metadata library in the database and is used in generating the subsequent new report, thereby increasing accuracy of the subsequent new report relative to previously-generated reports and the historical reports.

2. The report editor as in claim 1, wherein each statement of the series of statements comprise selectable qualifiers which alter a meaning of the statement.

3. The report editor as in claim 2, wherein the qualifiers are presented for selection in an order based on an associated probability of selection.

4. The report editor as in claim 1, wherein the stored reports in the database are presented in order of a score, the score being determined by matching metadata of the new report with metadata of the stored reports.

5. The report editor as in claim 1, wherein the stored reports in the database are presented in order of a score, the score being determined by matching the image of the new report with images of the stored reports.

6. The report editor as in claim 1, wherein the probability that a statement will be selected is based on a frequency of selection of the statement in the historical reports.

7. The report editor as in claim 1, wherein the non-transitory computer readable storage medium stores instructions for generating a medical report about a radiology image from a radiology report template, wherein the series of statements selectively included in the medical report include statements from a database of stored radiological reports.

8. The report editor as in claim 1, wherein the non-transitory computer readable storage medium stores instructions for generating the subsequent new report based on a selected report from the plurality of reports stored in the database including the stored completed report.

9. The report editor as in claim 1, wherein the non-transitory computer readable storage medium stores instructions for storing the edited statements from the completed report in the database.

10. The report editor as in claim 1, wherein the subsequent template for the subsequent new report is generated from a series of statements saved in the database, including the edited statements from the stored completed report.

11. The report editor as in claim 1, further comprising:
ranking the age of reports stored in the database such that newer reports have a higher ranking relative to older reports,
generating a score for each report saved in the database based on a degree of metadata matching and a ranking given to the metadata; and
presenting a list of reports in order of the generated scores.

12. The report editor as in claim 1, wherein each time the template is used to generate a subsequent new report, the accuracy at which the template presents the qualifiers is increased.

13. A report editor comprising:
a non-transitory computer readable storage medium; and
a database operatively engaged with the non-transitory computer readable storage medium;
wherein the non-transitory computer readable storage medium stores instructions for generating a report about an image from a template;
wherein the template comprises a series of statements selectively included in the report from the database;
wherein the database stores a plurality of reports including historical reports;
wherein a new report generated by the non-transitory computer readable storage medium is based on a selected report from the plurality of reports stored in the database;
wherein a selection of the series of statements in the new report is copied from a selection of statements in the selected report or from multiple stored reports;
wherein the series of statements is presented in an order corresponding to a probability that any particular statement is likely to be selected;
wherein the probability that the particular statement is selected is based on a selection of a first statement and a frequency of selection of a second statement when the first statement has been selected in the historical reports; or is based on the selection of a pair of statements and the frequency of selection of the second statement when the pair of statements has been selected in the historical reports;
wherein each statement of the series of statements comprises selectable qualifiers which alter a meaning of the statement;
wherein the qualifiers are presented for selection in an order based on an associated probability of selection;
wherein the probability of selection of a qualifier is stored in the template and is updated when a previous qualifier is selected;
wherein the selected series of statements in the new report are edited and the edited statements are stored in the database;
wherein the edited statements are included in a completed report and the completed report is stored in the database; and wherein the stored edited statements and the stored completed report update the database and are made available for use in a subsequent template for a subsequent new report.

14. The report editor as in claim 13, wherein the stored reports in the database are presented in order of a score, the score being determined by matching metadata of the new report with metadata of the stored reports.

15. The report editor as in claim 13, wherein the stored reports in the database are presented in order of a score, the score being determined by matching the image of the new report with images of the stored reports.

16. The report editor as in claim 13, wherein the probability that a statement will be selected is based on a frequency of selection of the statement in the historical reports.

17. The report editor as in claim 13, wherein the non-transitory computer readable storage medium stores instructions for generating a medical report about a radiology image from a radiology report template, wherein the series of statements selectively included in the medical report include statements from a database of stored radiological reports.

18. The report editor as in claim 13, wherein the non-transitory computer readable storage medium stores instructions for generating the subsequent new report based on a selected report from the plurality of reports stored in the database including the stored completed report.

19. The report editor as in claim 13, wherein the non-transitory computer readable storage medium stores instructions for storing the edited statements from the completed report in the database.

20. The report editor as in claim 13, wherein the subsequent template for the subsequent new report is generated from a series of statements saved in the database, including the edited statements from the stored completed report.

21. The report editor as in claim 13, wherein each time the template is used to generate a subsequent new report, the accuracy at which the template presents the qualifiers is increased.

22. The report editor as in claim 13, wherein anonymized metadata from each completed report is added to a statement metadata library in the database and is used in generating the subsequent new report, thereby increasing accuracy of the subsequent new report relative to previously-generated reports and the historical reports.

23. The report editor as in claim 13, further comprising:
ranking the age of reports stored in the database such that newer reports have a higher ranking relative to older reports,
generating a score for each report saved in the database based on a degree of metadata matching and a ranking given to the metadata; and
presenting a list of reports in order of the generated scores.

24. A report editor comprising:
a non-transitory computer readable storage medium; and
a database operatively engaged with the non-transitory computer readable storage medium;
wherein the non-transitory computer readable storage medium stores instructions for generating a report about an image from a template;
wherein the template comprises a series of statements selectively included in the report from the database;
wherein the database stores a plurality of reports including historical reports;

wherein a new report generated by the non-transitory computer readable storage medium is based on a selected report from the plurality of reports stored in the database;
wherein a selection of the series of statements in the new report is copied from a selection of statements in the selected report or from multiple stored reports;
wherein the series of statements are presented in order corresponding to a probability that any particular statement is likely to be selected;
wherein the probability that the particular statement is selected is based on a selection of a first statement and a frequency of selection of a second statement when the first statement has been selected in the historical reports; or is based on the selection of a pair of statements and the frequency of selection of the second statement when the pair of statements has been selected in the historical reports;
wherein the selected series of statements in the new report are edited and the edited statements are stored in the database;
wherein the edited statements are included in a completed report and the completed report is stored in the database; and
wherein the stored edited statements and the stored completed report update the database and are made available for use in a subsequent template for a subsequent new report and
ranking the age of reports stored in the database such that newer reports have a higher ranking relative to older reports,
generating a score for each report saved in the database based on a degree of metadata matching and a ranking given to the metadata; and
presenting a list of reports in order of the generated scores.

25. The report editor as in claim 24, wherein each statement of the series of statements comprise selectable qualifiers which alter a meaning of the statement.

26. The report editor as in claim 25, wherein the qualifiers are presented for selection in an order based on an associated probability of selection.

27. The report editor as in claim 24, wherein the stored reports in the database are presented in order of a score, the score being determined by matching metadata of the new report with metadata of the stored reports.

28. The report editor as in claim 24, wherein the stored reports in the database are presented in order of a score, the score being determined by matching the image of the new report with images of the stored reports.

29. The report editor as in claim 24, wherein the probability that a statement will be selected is based on a frequency of selection of the statement in the historical reports.

30. The report editor as in claim 24, wherein the non-transitory computer readable storage medium stores instructions for generating a medical report about a radiology image from a radiology report template, wherein the series of statements selectively included in the medical report include statements from a database of stored radiological reports.

31. The report editor as in claim 24, wherein the non-transitory computer readable storage medium stores instructions for generating the subsequent new report based on a selected report from the plurality of reports stored in the database including the stored completed report.

32. The report editor as in claim 24, wherein the non-transitory computer readable storage medium stores instructions for storing the edited statements from the completed report in the database.

33. The report editor as in claim 24, wherein the subsequent template for the subsequent new report is generated from a series of statements saved in the database, including the edited statements from the stored completed report.

34. The report editor as in claim 24, wherein each time the template is used to generate a subsequent new report, the accuracy at which the template presents the qualifiers is increased.

* * * * *